(12) United States Patent
Hsu et al.

(10) Patent No.: US 8,110,197 B2
(45) Date of Patent: Feb. 7, 2012

(54) **MUTATED *E. COLI* HEAT-LABILE ENTEROTOXIN**

(75) Inventors: Yu-Shen Hsu, Taipei County (TW); Young-Sun Lin, Taipei County (TW); Ta-Tung Yuan, San Marino, CA (US)

(73) Assignee: Development Center for Biotechnology, Xizhi (TW)

( * ) Notice: Subject to any disclaimer, the term of this patent is extended or adjusted under 35 U.S.C. 154(b) by 191 days.

(21) Appl. No.: 11/779,419

(22) Filed: Jul. 18, 2007

(65) Prior Publication Data

US 2008/0102078 A1    May 1, 2008

(30) Foreign Application Priority Data

Oct. 27, 2006 (TW) .............................. 95139707 A

(51) Int. Cl.
- *A61K 39/00* (2006.01)
- *A61K 39/02* (2006.01)
- *A61K 39/108* (2006.01)

(52) U.S. Cl. ............... 424/241.1; 424/184.1; 424/234.1; 424/236.1

(58) Field of Classification Search .................. None
See application file for complete search history.

(56) References Cited

U.S. PATENT DOCUMENTS

| | | |
|---|---|---|
| 4,596,792 A | 6/1986 | Vyas |
| 4,599,230 A | 7/1986 | Milich et al. |
| 4,599,231 A | 7/1986 | Milich et al. |
| 4,601,903 A | 7/1986 | Frasch |
| 2001/0044416 A1 * | 11/2001 | McCluskie et al. ............. 514/44 |
| 2004/0171565 A1 * | 9/2004 | Hone ............................. 514/44 |
| 2008/0102078 A1 | 5/2008 | Hsu et al. |

FOREIGN PATENT DOCUMENTS

| | | |
|---|---|---|
| JP | 04079898 | 3/1992 |
| WO | WO 99/47164 * | 9/1999 |
| WO | WO01/70257 | 9/2001 |

OTHER PUBLICATIONS

Cieplak et al. The Journal of Biological Chemistry vol. 270 p. 30545-30550, 1995.*
Harford et al. Eur. J. Biochem vol. 183(2):311-6, 1989.*
Domenighini et al. Mol Microbiol vol. 15(6):1165-7, 1995.*
Streatfield et al. PNAS vol. 89 (24): 12140-4, 1992.*
Non-Polio Enterovirus Infections, Sep. 5, 2006, obtained from the CDC website on May 28, 2007. http://www.cdc.gov/ncidod/dvrd/revb/enterovirus/non-polio_entero.htm.*
Svennerholm et al FEMS Immunol Med Microbiol vol. 50:146-156, 2007.*
Girard et al, Vaccine vol. 24: 4062-4081, 2006.*
Hepatitis C Fact Sheet Mar. 6, 2008—www.cdc.gov/hepatitis.*
Cieplak et al. "Site-Directed Mutagenic Alteration of Potential Active-site Residues of the A Subunit of *Escherichia Coli* Heat-Labile Enterotoxin, Evidence for a Catalytic Role for Glutmaic Acid 112"; Journal of Biological Chemistry, American Society for Biochemistry and Molecular Biology, Inc.; 270(51):30545-30550 (1995).

* cited by examiner

*Primary Examiner* — Oluwatosin Ogunbiyi

(74) *Attorney, Agent, or Firm* — Occhiuti Rohlicek & Tsao LLP

(57) ABSTRACT

This invention relates to a mutant *E. coli* heat-labile enterotoxin (LT) subunit A that can be used as an adjuvant. This subunit A mutant contains an amino acid substitution at a position corresponding to position 61 of a wild-type LT. An LT containing this mutated subunit A exhibits reduced toxicity compared to its wild type counterpart.

7 Claims, No Drawings

SEQUENCE LISTING

```
<160> NUMBER OF SEQ ID NOS: 15

<210> SEQ ID NO 1
<211> LENGTH: 777
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atgaaaaata taactttcat ttttttttatt ttattagcat cgccattata tgcaaatggc     60
gacaaattat accgtgctga ctctagaccc ccagatgaaa taaaacgttc cggaggtctt    120
atgcccagag ggcataatga gtacttcgat agaggaactc aaatgaatat taatctttat    180
gatcacgcga gaggaacaca aaccggcttt gtcagatatg atgacggata tgttaaaact    240
tctcttagtt tgagaagtgc tcacttagca ggacagtcta tattatcagg atattccact    300
tactatatat atgttatagc gacagcacca aatatgttta atgttaatga tgtattaggc    360
gtatacagcc ctcacccata tgaacaggag gtttctgcgt taggtggaat accatattct    420
cagatatatg gatggtatcg tgttaatttt ggtgtgattg atgaacgatt acatcgtaac    480
agggaatata gagaccggta ttacagaaat ctgaatatag ctccggcaga ggatggttac    540
agattagcag gtttcccacc ggatcaccaa gcttggagag aagaaccctg gattcatcat    600
gcaccacaag gttgtggaaa ttcatcaaga acaattacag gtgatacttg taatgaggag    660
acccagaatc tgagcacaat atatctcagg aaatatcaat caaaagttaa gaggcagata    720
ttttcagact atcagtcaga ggttgacata tataacagaa ttcggaatga attatga       777

<210> SEQ ID NO 2
<211> LENGTH: 240
<212> TYPE: PRT
<213> ORGANISM: Artificial Sequence
<220> FEATURE:
<223> OTHER INFORMATION: Description of Artificial Sequence: Synthetic
```

-continued

<400> SEQUENCE: 2

| Asn | Gly | Asp | Lys | Leu | Tyr | Arg | Ala | Asp | Ser | Arg | Pro | Asp | Glu | Ile |
|---|---|---|---|---|---|---|---|---|---|---|---|---|---|---|
| 1 | | | | 5 | | | | | 10 | | | | | 15 |

| Lys | Arg | Ser | Gly | Gly | Leu | Met | Pro | Arg | Gly | His | Asn | Glu | Tyr | Phe | Asp |
|---|---|---|---|---|---|---|---|---|---|---|---|---|---|---|---|
| | | | 20 | | | | | 25 | | | | | 30 | | |

| Arg | Gly | Thr | Gln | Met | Asn | Ile | Asn | Leu | Tyr | Asp | His | Ala | Arg | Gly | Thr |
|---|---|---|---|---|---|---|---|---|---|---|---|---|---|---|---|
| | | 35 | | | | | 40 | | | | | 45 | | | |

| Gln | Thr | Gly | Phe | Val | Arg | Tyr | Asp | Asp | Gly | Tyr | Val | Lys | Thr | Ser | Leu |
|---|---|---|---|---|---|---|---|---|---|---|---|---|---|---|---|
| | 50 | | | | | 55 | | | | | 60 | | | | |

| Ser | Leu | Arg | Ser | Ala | His | Leu | Ala | Gly | Gln | Ser | Ile | Leu | Ser | Gly | Tyr |
|---|---|---|---|---|---|---|---|---|---|---|---|---|---|---|---|
| 65 | | | | | 70 | | | | | 75 | | | | | 80 |

| Ser | Thr | Tyr | Tyr | Ile | Tyr | Val | Ile | Ala | Thr | Ala | Pro | Asn | Met | Phe | Asn |
|---|---|---|---|---|---|---|---|---|---|---|---|---|---|---|---|
| | | | | 85 | | | | | 90 | | | | | 95 | |

| Val | Asn | Asp | Val | Leu | Gly | Val | Tyr | Ser | Pro | His | Pro | Tyr | Glu | Gln | Glu |
|---|---|---|---|---|---|---|---|---|---|---|---|---|---|---|---|
| | | | 100 | | | | | 105 | | | | | 110 | | |

| Val | Ser | Ala | Leu | Gly | Gly | Ile | Pro | Tyr | Ser | Gln | Ile | Tyr | Gly | Trp | Tyr |
|---|---|---|---|---|---|---|---|---|---|---|---|---|---|---|---|
| | | 115 | | | | | 120 | | | | | 125 | | | |

| Arg | Val | Asn | Phe | Gly | Val | Ile | Asp | Glu | Arg | Leu | His | Arg | Asn | Arg | Glu |
|---|---|---|---|---|---|---|---|---|---|---|---|---|---|---|---|
| | 130 | | | | | 135 | | | | | 140 | | | | |

| Tyr | Arg | Asp | Arg | Tyr | Arg | Asn | Leu | Asn | Ile | Ala | Pro | Ala | Glu | Asp |
|---|---|---|---|---|---|---|---|---|---|---|---|---|---|---|
| 145 | | | | | 150 | | | | | 155 | | | | 160 |

| Gly | Tyr | Arg | Leu | Ala | Gly | Phe | Pro | Pro | Asp | His | Gln | Ala | Trp | Arg | Glu |
|---|---|---|---|---|---|---|---|---|---|---|---|---|---|---|---|
| | | | | 165 | | | | | 170 | | | | | 175 | |

| Glu | Pro | Trp | Ile | His | His | Ala | Pro | Gln | Gly | Cys | Gly | Asn | Ser | Ser | Arg |
|---|---|---|---|---|---|---|---|---|---|---|---|---|---|---|---|
| | | | | 180 | | | | | 185 | | | | | 190 | |

| Thr | Ile | Thr | Gly | Asp | Thr | Cys | Asn | Glu | Glu | Thr | Gln | Asn | Leu | Ser | Thr |
|---|---|---|---|---|---|---|---|---|---|---|---|---|---|---|---|
| | | 195 | | | | | 200 | | | | | 205 | | | |

| Ile | Tyr | Leu | Arg | Lys | Tyr | Gln | Ser | Lys | Val | Lys | Arg | Gln | Ile | Phe | Ser |
|---|---|---|---|---|---|---|---|---|---|---|---|---|---|---|---|
| | 210 | | | | | 215 | | | | | 220 | | | | |

| Asp | Tyr | Gln | Ser | Glu | Val | Asp | Ile | Tyr | Asn | Arg | Ile | Arg | Asn | Glu | Leu |
|---|---|---|---|---|---|---|---|---|---|---|---|---|---|---|---|
| 225 | | | | | 230 | | | | | 235 | | | | | 240 |

<210> SEQ ID NO 3
<211> LENGTH: 777
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

| atgaaaaata taactttcat ttttttttatt ttattagcat cgccattata tgcaaatggc | 60 |
|---|---|
| gacaaattat accgtgctga ctctagaccc ccagatgaaa taaaacgttc cggaggtctt | 120 |
| atgcccagag gcataatgag tacttcgat agaggaactc aaatgaatat taatctttat | 180 |
| gatcacgcga gaggaacaca accggctttt gtcagatatg atgacggata tgttagaact | 240 |
| tctcttagtt tgagaagtgc tcacttagca ggacagtcta tattatcagg atattccact | 300 |
| tactatatat atgttatagc gacagcacca aatatgttta atgttaatga tgtattaggc | 360 |
| gtatacagcc ctcacccata tgaacaggag gtttctgcgt taggtggaat accatattct | 420 |
| cagatatatg gatggtatcg tgttaatttt ggtgtgattg atgaacgatt acatcgtaac | 480 |
| agggaatata gagaccggta ttacagaaat ctgaatatag ctccggcaga ggatggttac | 540 |
| agattagcag gtttcccacc ggatcaccaa gcttggagag aagaaccctg gattcatcat | 600 |

```
gcaccacaag gttgtggaaa ttcatcaaga acaattacag gtgatacttg taatgaggag    660
acccagaatc tgagcacaat atatctcagg aaatatcaat caaaagttaa gaggcagata    720
ttttcagact atcagtcaga ggttgacata tataacagaa ttcggaatga attatga       777
```

<210> SEQ ID NO 4
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Asn Gly Asp Lys Leu Tyr Arg Ala Asp Ser Arg Pro Pro Asp Glu Ile
 1               5                  10                  15

Lys Arg Ser Gly Gly Leu Met Pro Arg Gly His Asn Glu Tyr Phe Asp
            20                  25                  30

Arg Gly Thr Gln Met Asn Ile Asn Leu Tyr Asp His Ala Arg Gly Thr
        35                  40                  45

Gln Thr Gly Phe Val Arg Tyr Asp Asp Gly Tyr Val Arg Thr Ser Leu
    50                  55                  60

Ser Leu Arg Ser Ala His Leu Ala Gly Gln Ser Ile Leu Ser Gly Tyr
65                  70                  75                  80

Ser Thr Tyr Tyr Ile Tyr Val Ile Ala Thr Ala Pro Asn Met Phe Asn
                85                  90                  95

Val Asn Asp Val Leu Gly Val Tyr Ser Pro His Pro Tyr Glu Gln Glu
            100                 105                 110

Val Ser Ala Leu Gly Gly Ile Pro Tyr Ser Gln Ile Tyr Gly Trp Tyr
        115                 120                 125

Arg Val Asn Phe Gly Val Ile Asp Glu Arg Leu His Arg Asn Arg Glu
    130                 135                 140

Tyr Arg Asp Arg Tyr Arg Asn Leu Asn Ile Ala Pro Ala Glu Asp
145                 150                 155                 160

Gly Tyr Arg Leu Ala Gly Phe Pro Pro Asp His Gln Ala Trp Arg Glu
                165                 170                 175

Glu Pro Trp Ile His His Ala Pro Gln Gly Cys Gly Asn Ser Ser Arg
            180                 185                 190

Thr Ile Thr Gly Asp Thr Cys Asn Glu Glu Thr Gln Asn Leu Ser Thr
        195                 200                 205

Ile Tyr Leu Arg Lys Tyr Gln Ser Lys Val Lys Arg Gln Ile Phe Ser
    210                 215                 220

Asp Tyr Gln Ser Glu Val Asp Ile Tyr Asn Arg Ile Arg Asn Glu Leu
225                 230                 235                 240
```

<210> SEQ ID NO 5
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Asn Gly Asp Lys Leu Tyr Arg Ala Asp Ser Arg Pro Pro Asp Glu Ile
 1               5                  10                  15

Lys Arg Ser Gly Gly Leu Met Pro Arg Gly His Asn Glu Tyr Phe Asp
            20                  25                  30

Arg Gly Thr Gln Met Asn Ile Asn Leu Tyr Asp His Ala Arg Gly Thr
```

```
                  35                  40                  45
Gln Thr Gly Phe Val Arg Tyr Asp Asp Gly Tyr Val Ser Thr Ser Leu
 50                  55                  60

Ser Leu Arg Ser Ala His Leu Ala Gly Gln Ser Ile Leu Ser Gly Tyr
 65                  70                  75                  80

Ser Thr Tyr Tyr Ile Tyr Val Ile Ala Thr Ala Pro Asn Met Phe Asn
                     85                  90                  95

Val Asn Asp Val Leu Gly Val Tyr Ser Pro His Pro Tyr Glu Gln Glu
                100                 105                 110

Val Ser Ala Leu Gly Gly Ile Pro Tyr Ser Gln Ile Tyr Gly Trp Tyr
                115                 120                 125

Arg Val Asn Phe Gly Val Ile Asp Glu Arg Leu His Arg Asn Arg Glu
                130                 135                 140

Tyr Arg Asp Arg Tyr Arg Asn Leu Asn Ile Ala Pro Ala Glu Asp
145                 150                 155                 160

Gly Tyr Arg Leu Ala Gly Phe Pro Pro Asp His Gln Ala Trp Arg Glu
                165                 170                 175

Glu Pro Trp Ile His His Ala Pro Gln Gly Cys Gly Asn Ser Ser Arg
                180                 185                 190

Thr Ile Thr Gly Asp Thr Cys Asn Glu Glu Thr Gln Asn Leu Ser Thr
                195                 200                 205

Ile Tyr Leu Arg Lys Tyr Gln Ser Lys Val Lys Arg Gln Ile Phe Ser
210                 215                 220

Asp Tyr Gln Ser Glu Val Asp Ile Tyr Asn Arg Ile Arg Asn Glu Leu
225                 230                 235                 240

<210> SEQ ID NO 6
<211> LENGTH: 1148
<212> TYPE: DNA
<213> ORGANISM: Escherichia coli

<400> SEQUENCE: 6
atgaaaaata taactttcat tttttttatt ttattagcat cgccattata tgcaaatggc      60
gacaaattat accgtgctga ctctagaccc ccagatgaaa taaaacgttc cggaggtctt     120
atgcccagag gcataatga gtacttcgat agaggaactc aaatgaatat taatctttat     180
gatcacgcga gaggaacaca aaccggcttt gtcagatatg atgacggata tgtttccact     240
tctcttagtt tgagaagtgc tcacttagca ggacagtcta tattatcagg atattccact     300
tactatatat atgttatagc gacagcacca aatatgttta atgttaatga tgtattaggc     360
gtatacagcc ctcacccata tgaacaggag gtttctgcgt aggtggaat accatattct     420 cagatatatg gatggtatcg tgttaatttt ggtgtgattg atgaacgatt acatcgtaac     480
agggaatata gagaccggta ttacagaaat ctgaatatag ctccggcaga ggatggttac     540
agattagcag gttccccacc ggatcaccaa gcttggagag aagaaccctg gattcatcat     600
gcaccacaag gttgtggaaa ttcatcaaga acaattacag gtgatacttg taatgaggag     660
acccagaatc tgagcacaat atatctcagg aaatatcaat caaagttaa gaggcagata     720 ttttcagact atcagtcaga ggttgacata tataacagaa ttcggaatga attatgaata     780
aagtaaaatg ttatgtttta tttacggcgt tactatcctc tctatgtgca tacggagctc     840
cccagtctat tacagaacta tgttcggaat atcgcaacac acaaatatat acgataaatg     900
acaagatact atcatatacg gaatcgatgg caggcaaaag agaaatggtt atcattacat     960
ttaagagcgg cgcaacattt caggtcgaag tcccgggcag tcaacatata gactcccaaa    1020
```

```
aaaaagccat tgaaaggatg aaggacacat taagaatcac atatctgacc gagaccaaaa    1080
ttgataaatt atgtgtatgg aataataaaa cccccaattc aattgcggca atcagtatgg    1140
aaaactag                                                             1148
```

<210> SEQ ID NO 7
<211> LENGTH: 777
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
atgaaaaata taactttcat tttttttatt ttattagcat cgccattata tgcaaatggc      60
gacaaattat accgtgctga ctctagaccc ccagatgaaa taaaacgttc cggaggtctt     120
atgcccagag ggcataatga gtacttcgat agaggaactc aaatgaatat taatctttat     180
gatcacgcga gaggaacaca aaccggcttt gtcagatatg atgacggata tgttcatact     240
tctcttagtt tgagaagtgc tcacttagca ggacagtcta tattatcagg atattccact     300
tactatatat atgttatagc gacagcacca aatatgttta atgttaatga tgtattaggc     360
gtatacagcc ctcacccata tgaacaggag gtttctgcgt taggtggaat accatattct     420
cagatatatg gatggtatcg tgttaatttt ggtgtgattg atgaacgatt acatcgtaac     480
agggaatata gagaccggta ttacagaaat ctgaatatag ctccggcaga ggatggttac     540
agattagcag gtttcccacc ggatcaccaa gcttggagag aagaaccctg gattcatcat     600
gcaccacaag gttgtggaaa ttcatcaaga acaattacag gtgatacttg taatgaggag     660
acccagaatc tgagcacaat atatctcagg aaatatcaat caaagttaa gaggcagata     720 ttttcagact atcagtcaga ggttgacata tataacagaa ttcggaatga attatga       777
```

<210> SEQ ID NO 8
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Asn Gly Asp Lys Leu Tyr Arg Ala Asp Ser Arg Pro Pro Asp Glu Ile
  1               5                  10                  15

Lys Arg Ser Gly Gly Leu Met Pro Arg Gly His Asn Glu Tyr Phe Asp
             20                  25                  30

Arg Gly Thr Gln Met Asn Ile Asn Leu Tyr Asp His Ala Arg Gly Thr
         35                  40                  45

Gln Thr Gly Phe Val Arg Tyr Asp Asp Gly Tyr Val His Thr Ser Leu
     50                  55                  60

Ser Leu Arg Ser Ala His Leu Ala Gly Gln Ser Ile Leu Ser Gly Tyr
 65                  70                  75                  80

Ser Thr Tyr Tyr Ile Tyr Val Ile Ala Thr Ala Pro Asn Met Phe Asn
                 85                  90                  95

Val Asn Asp Val Leu Gly Val Tyr Ser Pro His Pro Tyr Glu Gln Glu
            100                 105                 110

Val Ser Ala Leu Gly Gly Ile Pro Tyr Ser Gln Ile Tyr Gly Trp Tyr
        115                 120                 125

Arg Val Asn Phe Gly Val Ile Asp Glu Arg Leu His Arg Asn Arg Glu
    130                 135                 140
```

```
Tyr Arg Asp Arg Tyr Tyr Arg Asn Leu Asn Ile Ala Pro Ala Glu Asp
145                 150                 155                 160

Gly Tyr Arg Leu Ala Gly Phe Pro Pro Asp His Gln Ala Trp Arg Glu
            165                 170                 175

Glu Pro Trp Ile His His Ala Pro Gln Gly Cys Gly Asn Ser Ser Arg
        180                 185                 190

Thr Ile Thr Gly Asp Thr Cys Asn Glu Glu Thr Gln Asn Leu Ser Thr
    195                 200                 205

Ile Tyr Leu Arg Lys Tyr Gln Ser Lys Val Lys Arg Gln Ile Phe Ser
    210                 215                 220

Asp Tyr Gln Ser Glu Val Asp Ile Tyr Asn Arg Ile Arg Asn Glu Leu
225                 230                 235                 240

<210> SEQ ID NO 9
<211> LENGTH: 777
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
atgaaaaata taactttcat ttttttttatt ttattagcat cgccattata tgcaaatggc      60
gacaaattat accgtgctga ctctagaccc ccagatgaaa taaaacgttc cggaggtctt     120
atgcccagag ggcataatga gtacttcgat agaggaactc aaatgaatat taatctttat     180
gatcacgcga gaggaacaca aaccggcttt gtcagatatg atgacggata tgtttatact     240
tctcttagtt tgagaagtgc tcacttagca ggacagtcta tattatcagg atattccact     300
tactatatat atgttatagc gacagcacca aatatgttta atgttaatga tgtattaggc     360
gtatacagcc ctcacccata tgaacaggag gtttctgcgt taggtggaat accatattct     420
cagatatatg gatggtatcg tgttaatttt ggtgtgattg atgaacgatt acatcgtaac     480
agggaatata gagaccggta ttacagaaat ctgaatatag ctccggcaga ggatggttac     540
agattagcag gtttcccacc ggatcaccaa gcttggagag aagaaccctg gattcatcat     600
gcaccacaag ttgtggaaa ttcatcaaga acaattacag gtgatacttg taatgaggag     660
acccagaatc tgagcacaat atatctcagg aaatatcaat caaaagttaa gaggcagata     720
ttttcagact atcagtcaga ggttgacata tataacagaa ttcggaatga attatga       777

<210> SEQ ID NO 10
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asn Gly Asp Lys Leu Tyr Arg Ala Asp Ser Arg Pro Pro Asp Glu Ile
1               5                   10                  15

Lys Arg Ser Gly Gly Leu Met Pro Arg Gly His Asn Glu Tyr Phe Asp
            20                  25                  30

Arg Gly Thr Gln Met Asn Ile Asn Leu Tyr Asp His Ala Arg Gly Thr
        35                  40                  45

Gln Thr Gly Phe Val Arg Tyr Asp Asp Gly Tyr Val Tyr Thr Ser Leu
    50                  55                  60

Ser Leu Arg Ser Ala His Leu Ala Gly Gln Ser Ile Leu Ser Gly Tyr
```

```
                65                  70                  75                  80
Ser Thr Tyr Tyr Ile Tyr Val Ile Ala Thr Ala Pro Asn Met Phe Asn
                        85                  90                  95

Val Asn Asp Val Leu Gly Val Tyr Ser Pro His Pro Tyr Glu Gln Glu
                    100                 105                 110

Val Ser Ala Leu Gly Gly Ile Pro Tyr Ser Gln Ile Tyr Gly Trp Tyr
                115                 120                 125

Arg Val Asn Phe Gly Val Ile Asp Glu Arg Leu His Arg Asn Arg Glu
            130                 135                 140

Tyr Arg Asp Arg Tyr Tyr Arg Asn Leu Asn Ile Ala Pro Ala Glu Asp
145                 150                 155                 160

Gly Tyr Arg Leu Ala Gly Phe Pro Pro Asp His Gln Ala Trp Arg Glu
                165                 170                 175

Glu Pro Trp Ile His His Ala Pro Gln Gly Cys Gly Asn Ser Ser Arg
                180                 185                 190

Thr Ile Thr Gly Asp Thr Cys Asn Glu Glu Thr Gln Asn Leu Ser Thr
                195                 200                 205

Ile Tyr Leu Arg Lys Tyr Gln Ser Lys Val Lys Arg Gln Ile Phe Ser
        210                 215                 220

Asp Tyr Gln Ser Glu Val Asp Ile Tyr Asn Arg Ile Arg Asn Glu Leu
225                 230                 235                 240

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tctcaaacta agagaagttt taacatatcc gtcatcata                           39

<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
acttctcaaa ctaagagaag ttctaacata tccgtcatc                           39

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acttctcaaa ctaagagaag tgaaaacata tccgtcatc                           39

<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 14
acttctcaaa ctaagagaag tataaacata tccgtcatc                              39

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
acttctcaaa ctaagagaag tatgaacata tccgtcatc                              39
```

MUTATED E. COLI HEAT-LABILE ENTEROTOXIN

CROSS-REFERENCE TO RELATED APPLICATIONS

This application claims priority from Taiwanese Patent Application No. 95139707 filed Oct. 27, 2006, the content of which is incorporated herein by reference in its entirety.

BACKGROUND

Enterotoxigenic *Escherichia coli* strains cause diarrhea in humans and domestic animals by producing two types of enterotoxins, i.e., heat-labile toxin (LT) and heat-stable toxin (ST) (Hofstra et al., 1984, *J. Bio. Chem.* 259:15182-15187). LT is functionally, structurally, and immunologically related to cholera toxin (CT) (Clements et al., 1978, *Infect. Immun.* 21:1036-1039). LT and CT are synthesized as holotoxin molecules composed of five identical subunits B and an enzymatically active subunit A ($AB_5$) (Spangler, 1992, *Microbio. Rev.* 56(4):622-647). The B pentamer binds ganglioside GM1 in the membrane of intestinal epithelial cells or any other cell that contains GM1 (van Heyningen, 1974, *Science* 183:656-657). Following binding of subunits B to GM1 on the cell surface, subunit A is inserted into cytosal and proteolytically cleaved and reduced at its single disulfide bond to produce an enzymatically active A1 peptide and a smaller A2 peptide (Fishman PH, 1982, *J. Membr. Biol.* 69:85-97; Mekalanos et al., 1979, *J. Biol. Chem.* 254:5855-5861; Moss et al., 1981, *J. Biol. Chem.* 256:12861-12865). The A1 peptide is capable of binding NAD and catalyzing the ADP-ribosylation of Gsα, a GTP-binding regulatory protein associated with adenylate cyclase (Spangler, 1992, *Microbio. Rev.* 56(4):622-647). The resulting increase in cAMP eventually leads to the release of electrolytes and fluids from affected cells (Cheng et al., 2000, *Vaccine* 18:38-49).

LT has been shown to function as mucosal adjuvant and induce immune responses against mucosally co-administered antigens (Clements et al., 1988, *Vaccine* 6:269-277; Elson C O. 1989, *Immunol. Today* 146:29-33; Spangler, 1992, *Microbio. Rev.* 56(4):622-647). However, the high toxicity of wild-type LT has limited its clinical use. Thus, it is desirable to generate mutated LTs having reduced toxicity while retaining immunogenicity.

The term "*E. coli* heat-labile enterotoxin" or "LT" used herein refers to a heat-labile enterotoxin produced by any enterotoxigenic *E. coli* strain. The term "*E. coli* heat-labile enterotoxin subunit A" or "$LT_A$" refers to subunit A of LT. It includes both precursor $LT_A$, which contains a signal peptide, and mature $LT_A$ which has the signal peptide removed.

SUMMARY

This invention is based on the unexpected discovery that an LT containing a mutated $LT_A$ exhibits reduced toxicity compared to its wild type counterpart while retaining immunogenicity. This mutated $LT_A$ has an amino acid substitution at the position corresponding to position 61 of a wild-type $LT_A$, whose amino acid sequence, SEQ ID NO:5, is shown below.

Accordingly, this invention features an isolated polypeptide including a mutated $LT_A$ that contains an amino acid residue other than S, T, and F, at the position corresponding to position 61 of SEQ ID NO:5. The substituting amino acid residue can be D, E, H, I, K, L, N, P, Q, R, Y or W. It can be a naturally occurring amino acid or a non-naturally occurring amino acid, e.g., a D-amino acid or a β-amino acid. In one example, the $LT_A$ has the amino acid sequence of SEQ ID NO:2, 4, 8 or 10. An LT containing this mutated $LT_A$ exhibits reduced toxicity, i.e., <$10^{-5}$-fold that of a wild-type LT containing SEQ ID NO:5.

In another aspect, this invention features a vaccine containing an antigen and the mutated $LT_A$ described above. The vaccine can further include LT subunit B, which forms with the mutated $LT_A$ whole LT protein. The antigen can be derived from either a bacterium or a virus.

In yet another aspect, this invention features an isolated nucleic acid including a nucleotide sequence that encodes the above-described $LT_A$ mutant. In one example, the nucleotide sequence is SEQ ID NOs: 1, 3, 7, or 9. Also within the scope of this invention is a vector including the just-described nucleic acid and a transformed cell containing the vector.

The details of one or more embodiments of the invention are set forth in the description below. Other features, objects, and advantages of the invention will be apparent from the description and from the claims.

DETAILED DESCRIPTION

A detoxified LT, e.g., containing a mutated $LT_A$, is a desired vaccine adjuvant due to its high immunogenicity. The mutated $LT_A$ of this invention, designed to achieve this purpose, is made by introducing an amino acid substitution ir an $LT_A$ at a position corresponding to the position 61 of SEQ ID NO:5. $LT_A$ produced by different enterotoxigenic *E. coli* strains are highly homologous. Thus, by comparing the amino acid sequence of an $LT_A$ with SEQ ID NO:5, a skilled artisan can find out which position in this $LT_A$ corresponds to position 61 of SEQ ID NO:5. Just like the $LT_A$ of SEQ ID NO:5, almost all wild-type $LT_A$s include a serine at the position corresponding to position 61 of SEQ ID NO:5. An amino acid that is different from serine in, e.g., size or polarity, can be used as a substitutient substituent. Examples of the substituent amino acids include hydrophobic amino acid residues (e.g., I and L), charged amino acid residues (e.g., D, E, K, R, and H), or amino acid residues with bulky side chains (e.g., N, Q, Y, and W). Proline also can be used as a substituent as it generally alters the local structure of a polypeptide. These substituent amino acids include non-naturally occurring amino acids, e.g., D-amino acids or β-amino acids.

The $LT_A$ mutant of this invention can be prepared by methods well known in the art. For example, the mutant is produced by a recombinant method as follows. A cDNA that encodes a wild-type $LT_A$ is isolated from an enterotoxigenic *E. coli* strain and subjected to site-directed mutagenesis to produce a cDNA encoding the desired $LT_A$ mutant. See Ho et al., Gene, 77:51-59, 1989. The cDNA bearing the mutation is then inserted into an expression vector for transforming cells. Finally, the $LT_A$ mutant produced in the transformed cells is purified and assembled with LT subunit B to form whole LT protein.

The toxicity of an LT containing an $LT_A$ mutant described above can be assessed using assays such as the Y-1 adrenal cell assay. See Cheng et al., Vaccine, 18:38-49, 2000.

The $LT_A$ mutant of this invention can be used as an adjuvant in a vaccine. The vaccine (i.e., a human vaccine or a veterinary vaccine) can contain an antigen and the $LT_A$ mutant itself or an LT containing the $LT_A$ mutant. The antigen can be derived from a bacterium, e.g., *Streptococcus pyogenes, Streptococcus pneumoniae, Neiseria gonorrhoea, Neisseria meningitides, Corynebacterium diphtheriae, Clostridium botulinum, Clostridium perfringens, Clostridium tetani, Haemophilus influenzae, Klebsiella pneumoniae, Klebsiella ozaenae, Staphylococcus aureus, Vibrio cholerae, Escherichia* coli, *Pseudomonas aeruginosa, Campylobacter jejuni, Aeromonas hydrophila, Bacillus cereus, Yersinia enterocolitica, Yersinia pestis, Salmonella typhimurium, Treponema pallidum, Borrelia vincentii, Borrelia burgdorferi, Mycobacterium tuberculosis, Pneumocystis carinii, Mycoplasma* spp., *Rickettsia prowazeki, Chlamydia* spp., *Helicobacter pylori*. It also can be derived from a virus, e.g., influenza, herpes simplex virus, human immunodeficiency virus, cytomegalovirus, hepatitis c virus, delta hepatitis virus, poliovirus, hepatitis A virus, hepatitis B virus, Epstein-barr virus, varicella zoster virus, respiratory syncytial virus, enterovirus or Japanese encephalitis virus.

The vaccine can further contain a pharmaceutically acceptable carrier such as phosphate buffered saline or a bicarbonate solution. The carrier is selected on the basis of the mode and route of administration, and standard pharmaceutical practice. Suitable pharmaceutical carriers and diluents, as well as pharmaceutical necessities for their use, are described in Remington's Pharmaceutical Sciences.

Methods for preparing vaccines are generally well known in the art, as exemplified by U.S. Pat. Nos. 4,601,903; 4,599,231; 4,599,230; and 4,596,792. Vaccines may be prepared as injectables, as liquid solutions or emulsions. The antigen and the $LT_A$ mutant or the LT containing it may be mixed with physiologically acceptable excipients, which may include, water, saline, dextrose, glycerol, ethanol, and combinations thereof. The vaccine may further contain minor amounts of auxiliary substances such as wetting or emulsifying agents, or pH buffering agents to enhance the effectiveness of the vaccines. Vaccines may be administered parenterally, by injection subcutaneously or intramuscularly. Alternatively, other modes of administration including suppositories, oral, or topical formulations may be desirable. For suppositories, binders and carriers may include, for example, polyalkalene glycols or triglycerides. Oral formulations may include normally employed incipients such as, for example, pharmaceutical grades of saccharine, cellulose, magnesium carbonate and the like. These compositions take the form of solutions, suspensions, tablets, pills, capsules, sustained release formulations or powders.

The vaccine is administered in a manner compatible with the dosage formulation, and in an amount that is therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the polypeptide of this invention. Suitable regimes for initial administration and booster doses are also variable, but may include an initial administration followed by subsequent administrations. The dosage of the vaccine may also depend on the route of administration and varies according to the size of the host.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Example 1

Constructing Genes Encoding Wild Type $LT_A$ and LT Mutated $LT_A$

A 1.8-kb DNA fragment of an LT gene, including both subunit A and subunit B, was isolated from human entero-toxigenic *E. coli* H10407 and cloned into pBluescript II KS(−) vector (pBluescript-LThWT). The nucleotide sequence (SEQ ID NO:6) of the LT gene (encoding both Subunits A and B) and the amino acid sequence (SEQ ID NO:5) of subunit A of this LT are shown below:

```
Nucleotide sequence (SEQ ID NO: 6)of LT (Subunit
A: 1-777; Subunit B: 774-1148)
atgaaaaata taactttcat ttttttatt ttattagcat      60
cgccattata tgcaaatggc gacaaattat accgtgctga ctctagaccc ccagatgaaa    120
taaaacgttc cggaggtctt atgcccagag ggcataatga gtacttcgat agaggaactc    180
aaatgaatat taatctttat gatcacgcga gaggaacaca aaccggcttt gtcagatatg    240
atgacggata tgtttccact tctcttagtt tgagaagtgc tcacttagca ggacagtcta    300
tattatcagg atattccact tactatatat atgttatagc gacagcacca aatatgttta    360
atgttaatga tgtattaggc gtatacagcc ctcacccata tgaacaggag gtttctgcgt    420
taggtgaat accatattct cagatatatg gatggtatcg tgttaattt ggtgtgattg     480
atgaacgatt acatcgtaac agggaatata gagaccggta ttacagaaat ctgaatatag    540
ctccggcaga ggatggttac agattagcag gtttcccacc ggatcaccaa gcttggagag    600
aagaaccctg gattcatcat gcaccacaag gttgtggaaa ttcatcaaga acaattacag    660
gtgatacttg taatgaggag acccagaatc tgagcacaat atatctcagg aaatatcaat    720
caaaagttaa gaggcagata ttttcagact atcagtcaga ggttgacata tataacagaa    780
ttcggaatga attatgaata aagtaaaatg ttatgtttta tttacggcgt tactatcctc    840
tctatgtgca tacggagctc cccagtctat tacagaacta tgttcggaat atcgcaacac    900
acaaatatat acgataaatg acaagatact atcatatacg gaatcgatgg caggcaaaag    960
agaaatggtt atcattacat ttaagagcgg cgcaacattt caggtcgaag tcccgggcag   1020
tcaacatata gactcccaaa aaaaagccat tgaaaggatg aaggacacat taagaatcac   1080
atatctgacc gagaccaaaa ttgataaatt atgtgtatgg aataataaaa cccccaattc   1140
aattgcggca atcagtatg aaaactag
```

```
Amino acid sequence (SEQ ID NO: 5) of mature LTA
NGDKLYRADS RPPDEIKRSG GLMPRGHNEY FDRGTQMNIN LYDHARGTQT GFVRYDDGYV  60

STSLSLRSAH LAGQSILSGY STYYIYVIAT APNMFNVNDV LGVYSPHPYE QEVSALGGIP 120

YSQIYGWYRV NFGVIDERLH RNREYRDRYY RNLNIAPAED GYRLAGFPPD HQAWREEPWI 180

HHAPQGCGNS SRTITGDTCN EETQNLSTIY LRKYQSKVKR QIFSDYQSEV DIYNRIRNEL 240
```

Various $LT_A$ mutants were constructed using a site-directed mutagenesis method (Ho et al., 1989, *Gene* 77, 51-59). More specifically, $LT_A$ mutants, including $LT_A$(S61K), $LT_A$(S61R), $LT_A$(S61H), $LT_A$(S61Y) and $LT_A$(S61F) were constructed by replacing the serine at position 61 of SEQ ID NO:5 with K, R, H, Y, and F, respectively. The following oligonucleotide primers were used to construct these mutants: $LT_A$(S61K) [5' TCT CAA ACT AAG AGA AGT TTT AAC ATA TCC GTC ATC ATA 3'](SEQ ID NO:11), $LT_A$(S61R) [5' ACT TCT CAA ACT AAG AGA AGT TCT AAC ATA TCC GTC ATC 3'] (SEQ ID NO:12), $LT_A$(S61F) [5' ACT TCT CAA ACT AAG AGA AGT GAA AAC ATA TCC GTC ATC 3'](SEQ ID NO:13), $LT_A$ (S61Y) [5' ACT TCT CAA ACT AAG AGA AGT ATA AAC ATA TCC GTC ATC 3'](SEQ ID NO:14), $LT_A$(S61H) [5' ACT TCT CAA ACT AAG AGA AGT ATG AAC ATA TCC GTC ATC 3'](SEQ ID NO:15). The nucleotide sequences and amino acid sequences of these $LT_A$ are shown below:

```
Nucleotide sequence (SEQ ID NO: 1) of LTA(S61K)
atgaaaaata taactttcat tttttttatt ttattagcat      60
cgccattata tgcaaatggc gacaaattat accgtgctga ctctagaccc ccagatgaaa     120
taaaacgttc cggaggtctt atgcccagag ggcataatga gtacttcgat agaggaactc     180
aaatgaatat taatctttat gatcacgcga gaggaacaca aaccggcttt gtcagatatg     240
atgacggata tgttaaaact tctcttagtt tgagaagtgc tcacttagca ggacagtcta     300
tattatcagg atattccact tactatatat atgttatagc gacagcacca aatatgttta     360
atgttaatga tgtattaggc gtatacagcc ctcacccata tgaacaggag gtttctgcgt     420
taggtggaat accatattct cagatatatg gatggtatcg tgttaatttt ggtgtgattg     480
atgaacgatt acatcgtaac agggaatata gagaccggta ttacagaaat ctgaatatag     540
ctccggcaga ggatggttac agattagcag gtttcccacc ggatcaccaa gcttggagag     600
aagaaccctg gattcatcat gcaccacaag gttgtggaaa ttcatcaaga acaattacag     660
gtgatacttg taatgaggag acccagaatc tgagcacaat atatctcagg aaatatcaat     720
caaaagttaa gaggcagata ttttcagact atcagtcaga ggttgacata tataacagaa     777
ttcggaatga attatga Amino acid sequence (SEQ ID NO: 2) of LTA(S61K)
NGDKLYRADS RPPDEIKRSG GLMPRGHNEY FDRGTQMNIN      60
LYDHARGTQT GFVRYDDGYV

KTSLSLRSAH LAGQSILSGY STYYIYVIAT APNMFNVNDV     120
LGVYSPHPYE QEVSALGGIP
```

-continued

```
YSQIYGWYRV NFGVIDERLH RNREYRDRYY RNLNIAPAED     180
GYRLAGFPPD HQAWREEPWI

HHAPQGCGNS SRTITGDTCN EETQNLSTIY LRKYQSKVKR     240
QIFSDYQSEV DIYNRIRNEL

Nucleotide sequence (SEQ ID NO: 3) of LTA(S61R)
atgaaaaata taactttcat tttttttatt ttattagcat      60
cgccattata tgcaaatggc gacaaattat accgtgctga ctctagaccc ccagatgaaa     120
taaaacgttc cggaggtctt atgcccagag ggcataatga gtacttcgat agaggaactc     180
aaatgaatat taatctttat gatcacgcga gaggaacaca aaccggcttt gtcagatatg     240
atgacggata tgttagaact tctcttagtt tgagaagtgc tcacttagca ggacagtcta     300
tattatcagg atattccact tactatatat atgttatagc gacagcacca aatatgttta     360
atgttaatga tgtattaggc gtatacagcc ctcacccata tgaacaggag gtttctgcgt     420
taggtggaat accatattct cagatatatg gatggtatcg tgttaatttt ggtgtgattg     480
atgaacgatt acatcgtaac agggaatata gagaccggta ttacagaaat ctgaatatag     540
ctccggcaga ggatggttac agattagcag gtttcccacc ggatcaccaa gcttggagag     600
aagaaccctg gattcatcat gcaccacaag gttgtggaaa ttcatcaaga acaattacag     660
gtgatacttg taatgaggag acccagaatc tgagcacaat atatctcagg aaatatcaat     720
caaaagttaa gaggcagata ttttcagact atcagtcaga ggttgacata tataacagaa     777
ttcggaatga attatga Amino acid sequence (SEQ ID NO: 4) of LTA(S61R)
NGDKLYRADS RPPDEIKRSG GLMPRGHNEY FDRGTQMNIN      60
LYDHARGTQT GFVRYDDGYV

RTSLSLRSAH LAGQSILSGY STYYIYVIAT APNMFNVNDV     120
LGVYSPHPYE QEVSALGGIP

YSQIYGWYRV NFGVIDERLH RNREYRDRYY RNLNIAPAED     180
GYRLAGFPPD HQAWREEPWI

HHAPQGCGNS SRTITGDTCN EETQNLSTIY LRKYQSKVKR     240
QIFSDYQSEV DIYNRIRNEL

Nucleotide sequence (SEQ ID NO: 7) of LTA(S61H)
atgaaaaata taactttcat tttttttatt ttattagcat      60
cgccattata tgcaaatggc gacaaattat accgtgctga ctctagaccc ccagatgaaa     120
taaaacgttc cggaggtctt atgcccagag ggcataatga gtacttcgat agaggaactc     180
aaatgaatat taatctttat
```

-continued

```
gatcacgcga gaggaacaca aaccggcttt gtcagatatg    240
atgacggata tgttcatact
tctcttagtt tgagaagtgc tcacttagca ggacagtcta    300
tattatcagg atattccact
tactatatat atgttatagc gacagcacca aatatgttta    360
atgttaatga tgtattaggc
gtatacagcc ctcacccata tgaacaggag gtttctgcgt    420
taggtggaat accatattct
cagatatatg gatggtatcg tgttaatttt ggtgtgattg    480
atgaacgatt acatcgtaac
agggaatata gagaccggta ttacagaaat ctgaatatag    540
ctccggcaga ggatggttac
agattagcag gtttcccacc ggatcaccaa gcttggagag    600
aagaaccctg gattcatcat
gcaccacaag gttgtggaaa ttcatcaaga acaattacag    660
gtgatacttg taatgaggag
acccagaatc tgagcacaat atatctcagg aaatatcaat    720
caaaagttaa gaggcagata
ttttcagact atcagtcaga ggttgacata tataacagaa    777
ttcggaatga attatga
```

Amino acid sequence (SEQ ID NO: 8) of $LT_A$(S61H)

```
NGDKLYRADS RPPDEIKRSG GLMPRGHNEY FDRGTQMNIN     60
LYDHARGTQT GFVRYDDGYV

HTSLSLRSAH LAGQSILSGY STYYIYVIAT APNMFNVNDV    120
LGVYSPHPYE QEVSALGGIP

YSQIYGWYRV NFGVIDERLH RNREYRDRYY RNLNIAPAED    180
GYRLAGFPPD HQAWREEPWI

HHAPQGCGNS SRTITGDTCN EETQNLSTIY LRKYQSKVKR    240
QIFSDYQSEV DIYNRIRNEL
```

Nucleotide sequence (SEQ ID NO: 9) of $LT_A$(S61Y)

```
atgaaaaata taactttcat ttttttttatt ttattagcat     60
cgccattata tgcaaatggc
gacaaattat accgtgctga ctctagaccc ccagatgaaa    120
taaaacgttc cggaggtctt
atgcccagag ggcataatga gtacttcgat agaggaactc    180
aaatgaatat taatctttat
gatcacgcga gaggaacaca aaccggcttt gtcagatatg    240
atgacggata tgtttatact
tctcttagtt tgagaagtgc tcacttagca ggacagtcta    300
tattatcagg atattccact
tactatatat atgttatagc gacagcacca aatatgttta    360
atgttaatga tgtattaggc
gtatacagcc ctcacccata tgaacaggag gtttctgcgt    420
taggtggaat accatattct
cagatatatg gatggtatcg tgttaatttt ggtgtgattg    480
atgaacgatt acatcgtaac
agggaatata gagaccggta ttacagaaat ctgaatatag    540
ctccggcaga ggatggttac
agattagcag gtttcccacc ggatcaccaa gcttggagag    600
aagaaccctg gattcatcat
gcaccacaag gttgtggaaa ttcatcaaga acaattacag    660
gtgatacttg taatgaggag
acccagaatc tgagcacaat atatctcagg aaatatcaat    720
caaaagttaa gaggcagata
```

-continued

```
ttttcagact atcagtcaga ggttgacata tataacagaa    777
ttcggaatga attatga
```

Amino acid sequence (SEQ ID NO: 10) of $LT_A$(S61Y)

```
NGDKLYRADS RPPDEIKRSG GLMPRGHNEY FDRGTQMNIN     60
LYDHARGTQT GFVRYDDGYV

YTSLSLRSAH LAGQSILSGY STYYIYVIAT APNMFNVNDV    120
LGVYSPHPYE QEVSALGGIP

YSQIYGWYRV NFGVIDERLH RNREYRDRYY RNLNIAPAED    180
GYRLAGFPPD HQAWREEPWI

HHAPQGCGNS SRTITGDTCN EETQNLSTIY LRKYQSKVKR    240
QIFSDYQSEV DIYNRIRNEL
```

For comparison, another LT mutant, LTp(S63K), derived from EWDB299 (Dallas et al., 1979, *J. Bacteriol.* 139, 850-859) was also constructed by replacement of serine at amino acid position 63 of subunit A with lysine.

Example 2

Preparing Wild Type LT and LT Containing Mutated $LT_A$ pBluescript II KS(−) vectors containing native or mutant LT genes, including genes for both subunit A and subunit B, were transformed into *E. coli* HB101. The native and mutant LT's were purified from cultures grown overnight in a 3-liter flask containing L-broth supplemented with 100 μg of ampicillin per ml. The cells were harvested by centrifugation, resuspended in TEAN buffer (0.2 M NaCl, 50 mM Tris, 1 mM EDTA and 3 mM NaN3, pH 7.4), and lysed with microfluidizer (Microfluidics Corporation, USA). After the lysates were clarified by centrifugation, the LT was fractionated by adding solid ammonium sulfate to 65% saturation. The preparation was then suspended in TEAN buffer, dialyzed thoroughly against the same buffer and used as the crude LT. The crude LT was subjected to chromatography on Immobilized D-galactose (Pierce, Rockford, Ill.) columns equilibrated with TEAN buffer at 4° C. (Uesaka et al., 1994, *Microbial Pathogenesis* 16:71-76). Native and mutant LT's were eluted with 0.3 M galactose in TEAN. Each purified toxin was dialyzed against PBS buffer for biological and immunological assays.

The purified wild-type and mutant LT were separated by SDS-PAGE, wherein the molecular weight of LT subunit A was about 28 to 29 kDa, and the molecular weight of LT subunit B was about 12 to 13 kDa. The yields of the entire LT containing $LT_A$(S61K), i.e., LTh(S61K), and $LT_A$(S61R), i.e., LTh(S61R) were similar to the LT containing the $LT_A$ of SEQ ID NO:5.

$AB_5$ heterohexamers and $B_5$ pentamers of the LT were separated by pH 3-10 isoelectric focusing gel (invitrogen). Intensity of AB5 and B5 protein bands was assayed by UVIBand software (UVItec Limited) to calculate the percentage of the $AB_5$ heterohexamers and the $B_5$ pentamers (The isoelectric point (pI) value of $AB_5$ was between 8.0 and 7.8, and the pI value of $B_5$ was between 8.3 and 8.1), the results are listed in Table 1.

TABLE 1

Preparation of wild-type LT and LT containing mutated $LT_A$

| *E. coli* heat-labile enterotoxin (LT) | The ratio of AB5/AB5 + B5 (%) |
|---|---|
| LTh(WT) | 91 (%) |
| LTh(S61K) | 92 (%) |

TABLE 1-continued

Preparation of wild-type LT and LT containing mutated $LT_A$

| E. coli heat-labile enterotoxin (LT) | The ratio of AB5/AB5 + B5 (%) |
|---|---|
| LTh(S61R) | 85 (%) |
| LTh(S61H) | 60 (%) |
| LTh(S61F) | 70 (%) |
| LTh(S61Y) | 57 (%) |

The percentages of $AB_5$ of purified LTh(S61K) and LTh(S61R) were about 90-100%.

Example 3

Determining Effect of Wild-Type LT and LT Containing Mutated $LT_A$ on Intracellular cAMP Levels Caco-2 cells (ATCC HTB-37) were maintained in MEM-α medium supplemented with 20% FBS in 24-well plate at a concentration of 5×104 cells per well, grown to near confluency, and incubated in MEM-α containing 1% FBS and 1 mM 3-isobutyl-1-methylxanthine (IBMX) for 30 min in 5% CO2 prior to addition of toxins (Grant et al., 1994, Infection and Immunity 62: 4270-4278). Native or mutant LT was added to each well and incubated for 4 hours. The cells were then washed twice with cold PBS. Intracellular cAMP was extracted by adding 200 μl of 0.1 N HCl to each well and incubated at room temperature for 15 minutes. Supernatant of cell lysates were collected following addition of 0.1 N NaOH to each well. (Cheng et al., 2000, Vaccine 18: 38-49; Park et al., 1999, Experimental and Molecular Medicine 31: 101-107). cAMP was measured with a cAMP enzyme immunoassay kit (Assay designs; Correlate-EIA). Results obtained from this example show that LTh(S61K) did not increase the concentration of intracellular cAMP.

Example 4

Determining Toxicity of LT Containing Mutated $LT_A$ using Y1 Adrenal Tumor Cell Assay In this study, LT samples, including wild-type LT, LT active site mutant (h61K), and LT subunit B complex, B5, were evaluated for enterotoxic effect. Mouse Y-1 adrenal tumor cells (ATCC CCL-79) maintained in Ham's F12 media supplemented with 15% horse serum, 2.5% fetal bovine serum, 2 mM L-glutamine, and 1.5 g/L sodium bicarbonate were seeded in 96-well flat-bottom plates at a concentration of 2×104 cells per well (200 ul/well) at 37° C. in 5% CO2 for 48 hrs. Cells in 96-well flat-bottom plates were washed twice with 1×PBS (pH 7.4) and then treated with serially diluted LT samples (10 μg/200 μl~10–10 μg/200 μl) at 37° C. in 5% CO2 overnight. Cells were examined by light microscopy for typical cell rounding 24 hrs after toxin treatment. Activity is defined as the minimum concentration of the toxin required to initiate cell rounding (ECi) or the toxin concentration required for 50% cell rounding (EC50). See David et al., 1975, Infection and Immunity, 11:334-336; Cheng et al., 1999, Vaccine 18:38-49. The toxicity of LTh(S61K), LTh (S61R), LTh(S61H) is significantly lower compared to wild-type LT, i.e., $10^{-6}$ versus 1. See Table 2 below. The toxicity of LTh(S61F) is also lower (i.e., $10^{-5}$), but the reduction is not as significant as the other mutants.

TABLE 2

Toxicity of LT containing wild-type or mutated $LT_A$

| E. coli heat-labile enterotoxin (LT) | The amount of LT (pg/well) | Toxic intensity (wild type LT is 1) |
|---|---|---|
| LTh(WT) | 0.1 | 1 |
| LTh(S61K) | 100,000 | $10^{-6}$ |
| LTh(S61R) | 100,000 | $10^{-6}$ |
| LTh(S61H) | 100,000 | $10^{-6}$ |
| LTh(S61F) | 10,000 | $10^{-5}$ |
| LTh(S61Y) | 100,000 | $10^{-6}$ |
| LTh(S63K) | 10,000 | $10^{-5}$ |

Example 5

Determining Toxicity of LT Containing Mutated $LT_A$ by Rabbit Ileal Loop Assay The assay was performed as previously described (Giannelli et al., 1997, Infection and Immunity 65: 331-334; Giuliani et al., 1998, J. Exp. Med. 187:1123-1132). The New Zealand adult rabbits, ~2.5 Kg each, were used for this assay. Loops, each 5 cm long, were made by starting at the end of the rabbit's small intestines and moving toward the stomach. 0.5 ml samples with various amounts of LT or LT mutants were injected intro each loop and then the abdomen was closed. After 18 hours, the liquid accumulated in each loop was collected and measured. The experiment was performed three times and the results expressed in milliliters per centimeter. Results from this experiment show that 500 μg of LTh(S61K) only accumulated 1 ml fluid in the rabbit ileal loop, and the volume of the accumulated fluid was similar to native control. When 0.1 μg of wild-type LT was used, the volume of accumulated fluid of wild-type LT was considerably larger than that of LTh(S61K). In addition, the fluid accumulation of other LTp(S63K) also considerably larger than that of LTh (S61K).

Example 6

Determining Adjuvant Effect of LT Containing Mutated $LT_A$ in Intranasal Immunization Deactivated Influenza virus, A/Puerto Rico/8/34 (H1N1) (PR8) (ATCC VR-95), was used in this example. The viral particles were prepared as previously described in (Aitken et al., 1980, *Eur. J. Biochem.* 107:51-56; Gallagher et al., 1984, *J. Clin. Microbiol.* 20:89-93; Johansson et al., 1989, *J. Virol.* 63:1239-1246). Briefly, the virus was propagated in the allantoic cavity of 10-day-old embryonated hen's eggs at 35° C. for two days. The allantoic fluid from eggs infected with PR8 was first centrifuged at low-speed and then centrifuged at 96,000×g for 1 hour to precipitate viral particles, which were resuspended in phosphate-buffered saline (PBS). These particles were loaded onto a 30-60% sucrose density gradient and centrifuged for 5 hours at 96,000×g. The fraction containing the virus was collected and diluted with PBS. The virus was further pelleted at 96,000×g for 1 hour and resuspended in PBS. Purified virus was treated with 0.025% formalin at 4° C. for a week. Protein concentration was measured and standardized based on the optical density, Bio-Rad Protein Assay, and the haemagglutinin (HA) content was determined by SDS-polyacryamide gel electrophoresis (Oxford et al., 1981, *J. Biol. Stand.* 9:483-491).

Female BALB/c mice, between 6 and 8 weeks old, were obtained from Taiwan National Laboratory Animal Center.

Groups consisting of five of mice each were immunized intranasally with 25 μl PBS containing 20 μg of inactivated influenza virus (flu.Ag) alone or in combination with 8 μg of native or mutant LT under anesthesia. The mice were re-immunized 3 weeks later. Control mice were given PBS under the same condition. Two weeks after the final immunization, mice in each group were sacrificed to obtain serum and conduct haemagglutination inhibition (HI) assay. Significantly enhanced HI titers were detected in mice intranasally immunized with the inactivated virus vaccine in combination with LTh(S61K) or LTp(S63K) when compared with mice intranasally immunized with inactivated virus vaccine alone. The HI titer of LTh(S61K) in combination with the inactivated virus was substantially increased. The HI titer of LTh(S61K) in combination with the virus is 813, similar to that of LTh (S63K) in combination with the virus but larger than that of the virus alone.

Example 7

Determining Adjuvant Effect of LT Containing Mutated $LT_A$ in Intramuscular Immunization The procedure carried out in Example 6 was repeated except that the immunization utilizes intramuscular delivery. Intramuscular vaccines were prepared in 50 μl PBS containing 10 μg of inactivated virus vaccine alone or in combination with 4 μg of native or mutant LT and were injected into the posterior thigh muscle. The immunization and sampling programs were performed as described. The HI titer of LTh (S61K) in combination with the inactivated virus was substantially increased. The HI titer of LTh(S61K) in combination with the virus was 512, which is significantly higher than that of wild type LT in combination with the virus or that of the virus alone.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A detoxified *E. coli* heat-labile enterotoxin, comprising a mutated subunit A containing only one mutated residue as compared to its wild-type counterpart, the mutated residue being K and located at the position corresponding to position 61 of SEQ ID NO:5; and

*E. coli* heat-labile enterotoxin subunit B, wherein the detoxified *E. coli* heat-labile enterotoxin is in $AB_5$ format, and wherein detoxified *E. coli* heat-labile enterotoxin proteins purified from an *E. coli* expressing the mutated subunit A and *E. coli* heat-labile enterotoxin subunit B are in the $AB_5$ format and the $B_5$ format, the $AB_5/AB_5+B_5$ ratio being at least 1.3 fold greater than the $AB_5/AB_5+B_5$ ratio of detoxified *E. coli* heat-labile enterotoxin proteins purified from an *E. coli* expressing a mutated *E. coli* heat-labile enterotoxin subunit A having F at the position, corresponding to position 61 of SEQ ID NO:5 and *E. coli* heat-labile enterotoxin subunit B.

2. The detoxified *E. coli* heat-labile enterotoxin of claim 1, wherein the mutated subunit A includes the amino acid sequence of SEQ ID NO:2.

3. An immune composition, comprising an antigen and the detoxified *E. coli* heat-labile enterotoxin of claim 1 as an adjuvant.

4. The immune composition of claim 3, wherein the detoxified *E. coli* heat-labile enterotoxin contains a mutated subunit A that includes the amino acid sequence of SEQ ID NO:2.

5. The immune composition of claim 3, wherein the antigen is from a bacterium or a virus.

6. The immune composition of claim 5, wherein the antigen is from a bacterium selected from the group consisting of *Streptococcus pneumoniae, Escherichia coli, Neisseria meningitidis*, and *Haemophilus influenzae* b.

7. The immune composition of claim 5, wherein the antigen is from a virus selected from the group consisting of influenza virus, hepatitis A virus, hepatitis B virus, human papillomavirus, poliovirus, and rotavirus.

* * * * *